US006303799B1

(12) United States Patent
Cheng et al.

(10) Patent No.: US 6,303,799 B1
(45) Date of Patent: Oct. 16, 2001

(54) POLYNUCLEOTIDE CROSSLINKING AGENTS

(75) Inventors: Peter C. Cheng, San Jose; David Albagli, Menlo Park; Michael L. Wood, Mountain View, all of CA (US)

(73) Assignee: Naxcor, Menlo Park, CA (US)

( * ) Notice: Subject to any disclaimer, the term of this patent is extended or adjusted under 35 U.S.C. 154(b) by 0 days.

(21) Appl. No.: 09/189,294

(22) Filed: Nov. 10, 1998

(51) Int. Cl.[7] ............... C07D 317/44; C07D 307/78; C07D 277/22; C07H 19/00; C07H 21/04
(52) U.S. Cl. ............... 549/441; 435/6; 435/91.1; 536/22.1; 536/23.1; 536/25.3; 536/24.3; 549/467; 548/203; 548/495; 558/254
(58) Field of Search .............. 435/6, 91.1; 536/22.1, 536/23.1, 24.3, 25.3; 549/441, 467; 548/203, 495; 558/254

(56) References Cited

U.S. PATENT DOCUMENTS

| 4,599,303 | 7/1986 | Yabusaki et al. ............... 435/6 |
| 4,826,967 | 5/1989 | Glass ............... 536/23 |
| 5,082,934 | 1/1992 | Saba et al. ............... 536/17.6 |
| 5,112,963 | 5/1992 | Pieles et al. ............... 536/27 |
| 5,489,678 | 2/1996 | Fodor et al. ............... 536/22.1 |
| 5,539,082 | 7/1996 | Nielsen et al. ............... 530/300 |
| 5,616,464 | 4/1997 | Albagli et al. ............... 435/6 |
| 5,646,313 | * 7/1997 | Danvy et al. ............... 549/441 |
| 5,652,096 | 7/1997 | Cimino ............... 435/6 |
| 5,705,333 | 1/1998 | Shah et al. ............... 435/6 |
| 5,744,101 | 4/1998 | Fodor et al. ............... 422/131 |
| 5,767,259 | 6/1998 | Albagli et al. ............... 536/23.1 |
| 5,773,571 | 6/1998 | Nielsen et al. ............... 530/300 |
| 5,789,385 | * 8/1998 | Anderson et al. ............... 514/25 |

FOREIGN PATENT DOCUMENTS

| 3804243 A1 | 8/1989 | (DE) . |
| 0 130 523 A2 | 1/1985 | (EP) . |
| 0 324 616 A3 | 7/1989 | (EP) . |
| WO 94/24120 | 10/1994 | (WO) . |
| WO 96/28438 | 9/1996 | (WO) . |
| WO 96/34984 | 11/1996 | (WO) . |
| WO98/39280 | * 9/1998 | (WO) . |

OTHER PUBLICATIONS

Misiura et al., "Biotinyul and phosphotyrosinyl phosphoramidite derivatives useful in the incorporation of multiple reporter groups on synthetic oligonucleotides," *Nucleic Acids Research*, 18:4345–4354 (1990).
Zehnder et al., "Cross–linking hybridization assay for direct detection of factor V Leiden mutation," *Clinical Chemistry*, 43:1703–1708 (1997).

* cited by examiner

*Primary Examiner*—Jezia Riley
(74) *Attorney, Agent, or Firm*—Heller Ehrman White & McAuliffe LLP

(57) ABSTRACT

Novel aryl derivatives comprising an aryl olefin moiety linked to a non-nucleosidic backbone moiety are disclosed. The resulting molecules are typically used as photoactivated crosslinking groups when incorporated into oligonucleotides to crosslink nucleic acid strands.

37 Claims, 2 Drawing Sheets

POLYNUCLEOTIDE CROSSLINKING AGENTS

FIELD OF THE INVENTION

This invention is related to photoactive compounds that can be incorporated into synthetic oligonucleotides to crosslink nucleic acid strands.

DESCRIPTION OF RELATED ART

The use of crosslinkable probes in nucleic acid hybridization assays to crosslink to target sequences is demonstrated in U.S. Pat. No. 4,826,967 by R. Glass the crosslinking compounds are based on furocoumarin (or psoralen) attached to existing polynucleotides (usually through adduct formation) and are satisfactory for many applications. However, the crosslinking group/nucleoside adduct is difficult to synthesize, particularly in large quantities.

In U.S. Pat. No. 5,082,934, Saba et al. describe a photoactivatible nucleoside analogue comprising a coumarin moiety linked through its phenyl ring to the 1-position of a ribose or deoxyribose sugar moiety in the absence of an intervening base moiety. The resulting nucleoside analogue is used as a photo-crosslinking group when inserted into a polynucleotide as a replacement for one or more of the complementary nucleoside bases present in a probe used in hybridization assays. However, the sugar moiety limits the conformational flexibility of the crosslinking moiety.

In PCT Publication Number WO96/28438, Wood et al. describe photoactivatible non-nucleosidic coumarin derivatives wherein the coumarin moiety is joined within the backbone of an oligonucleotide probe via moieties other than deoxyribose or ribose. The stability and reactivity of these compounds are particularly useful for nucleic acid diagnostic assays and therapeutics because of the rapid crosslinking reaction between the coumarin moiety and the natural bases found in the opposite strand.

Nevertheless, there remain applications for crosslinkable probes in which reaction with a natural base is not desirable, but instead reaction between two non-natural reactants is the desired mode.

SUMMARY OF THE INVENTION

The current invention provides non-nucleosidic, stable, photoactive compounds that can be used as photo-crosslinking reagents in nucleic acid hybridization assays and therapeutic applications, as well as probes incorporating the compounds.

The compounds comprise aryl olefin derivatives prepared by linking the aryl moiety to a functionalized saturated or unsaturated hydrocarbon molecule, such as glycerol. The functionalized hydrocarbon moiety of the resulting compound is equivalent to the sugar of a nucleoside, while the aryl olefin moiety occupies the position of a base. Accordingly, the compounds can be inserted into growing polynucleotide chains using automated or manual techniques of polynucleotide synthesis. The double bond of the aryl olefin is a photoactive group that covalently crosslinks to suitable reactants in the complementary strand when an oligonucleotide containing this crosslinkable non-nucleoside analogue (the "probe") is used in a hybridization assay and/or therapeutic application.

The photoactive compound has the formula where V is

Y is H, F, lower alkyl, lower alkoxy, or lower fluoroalkyl,

Z is O or S;

$R_1$ is H, R', —OR', —SR', or —NR'R" in which R' and R" independently represent H, lower alkyl, haloalkyl, alkoxy, alkylcarbonyl, or aryl, heteroaryl, or polycyclic aryl, each optionally substituted with W;

$R_2$ is aryl, heteroaryl or polycyclic aryl, each optionally substituted with W;

B represents (1) a linear, branched, or cyclic hydrocarbon group containing from 2 to 10 carbon atoms and, if cyclic, containing a 5- or 6-membered ring or (2) a heterocyclic aromatic ring system containing a 5- or 6-membered ring, said B(1) or B(2) being substituted with 1, 2, or 3 groups of the formula $R_3$, wherein $R_3$ independently represents H, OH, $NH_2$, or COOH, or a protecting or coupling group capable of protecting or coupling a functional group during synthesis of a polynucleotide, or $R_3$ represents a nucleotide or a polynucleotide and wherein one to three carbon atoms of the hydrocarbon group can be replaced by an oxygen, nitrogen, or sulfur atom; except that B is not ribose or deoxyribose;

X represents (1) a bond, (2) a linear, branched, or cyclic hydrocarbon group containing 1 to 10 carbon atoms, in which optionally one to three carbon atoms of the hydrocarbon group are replaced by an oxygen, sulfur, or nitrogen atom wherein X is optionally substituted with 1–3 substituents selected from the group consisting of hydroxy, halogen, amino, amido, azido, carboxy, carbonyl, perfluoromethyl, and cyano functional groups; and wherein X is attached to the phenyl ring of said formula directly or through W;

n is 0, 1, 2, or 3;

each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two Ws together can represent a ring fused to the phenyl ring of said formula;

with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer.

DESCRIPTION OF SPECIFIC EMBODIMENTS

The present invention provides crosslinkable compounds that can be used as a photoactivatible non-nucleosidic crosslinker in oligonucleotide probes in hybridization assays and/or therapeutic applications. In nucleic acid diagnostic assays, the compounds of the inventions are typically used as part of synthetic DNA or RNA oligonucleotides to determine the presence or absence of a specific DNA or RNA base sequence in a sample. More specifically, this invention provides photoactive aryl olefins attached to a stable, flexible, functionalized hydrocarbon backbone unit that act as photoactive crosslinking compounds in hybridization assays.

The compounds of the invention have the general formula:

The crosslinking moiety is an aryl olefin derivative wherein the crosslinking group (an activated double bond) is located in the right orientation and at the right distance to crosslink with a non-nucleosidic reactant in the opposite strand.

The linking moiety will normally be formed from a precursor that contains from 1 to 100, preferably 1 to 25, more preferably 1 to 10, atoms with functional groups at two locations for attaching the other moieties to each other. After reaction of the precursor to form the linking moiety, the total number of atoms in the shortest linking chain of atoms between the ring system of the aryl olefin and the backbone moiety (sugar substitute) is generally from 1 to 15, preferably 1 to 7, more preferably 1 to 3. Otherwise this part of the structure can vary widely, as this is essentially just a flexible linkage from the crosslinking moiety to the backbone moiety.

The linking moiety is most often a stable cyclic or acyclic moiety derived by reaction of a molecule bearing appropriate functional groups for linking the crosslinking molecule at one end and the backbone molecule at the other end. However, if sufficient functional groups are present in the backbone and crosslinking moieties, a precursor to the linking moiety need not be used (i.e., the backbone and crosslinking moieties can be connected by a covalent bond).

The backbone moiety, so called because it ultimately functions in place of the ribose or deoxyribose portion of the backbone of a polynucleotide, will generally have 1 to 3 (sometimes more) hydroxyl groups (or similar functional groups, as discussed below) attached to different carbon atoms. The backbone moiety is generally uncharged so that it can function as a substitute for ribose or deoxyribose in the final modified nucleotide. Backbone moieties include but are not limited to the following: (1) linear hydrocarbon moieties such as ethyl or propyl or a longer hydrocarbon chain with appropriate functional groups, usually selected from the group consisting of —OH, —NH$_2$, —SH, —COOH, acid halides, and acid anhydrides, and (2) cyclic hydrocarbon moieties typically having a 5- to 7-membered carbon ring structure bearing one to three hydroxyl group or other functional groups as in (1) above. The reactive functional groups mentioned above (other than —OH and —SH) are generally present only in intermediates; however, after reacting with other functional groups, they become stable groups or form covalent bonds to other parts of the molecule.

In addition to the basic structure described above, one or more coupling moieties can be attached to the backbone moiety to facilitate formation of bonds to existing or growing polynucleotide chains. The coupling moieties will typically comprise hydroxy coupling and/or protecting groups that are used in solution or solid-phase nucleic acid synthesis when the molecule in question is an intermediate being used in the preparation of a probe molecule. Typical coupling groups include phosphoramidite, phosphate, triphosphate, H-phosphonate, and methyl phosphonamidite; typical protecting groups include trityl, dimethoxytrityl, monomethoxytrityl, pixyl, t-butoxycarbonyl (Boc), fluorenylmethoxycarbonyl (Fmoc), 6-nitroveratryl, 6'-nitropiperonyl, pyrenylmethyl, methyl-6-nitroveratryl, and methyl-6-nitropiperonyl groups. Non-phosphorous coupling groups include carboxy groups, carbamates, amides, amines and linear and cyclic hydrocarbon groups. For a review of such chemistry, see "Oligonucleotide Synthesis, A Practical Approach," M. J. Gait, ed., IRL Press Ltd., Oxford, Great Britain, 1984, which is herein incorporated by reference. Light activated protecting groups are disclosed in Fodor, et al., U.S. Pat. Nos. 5,489,678 and 5,744,101. Amide backbones are disclosed in U.S. Pat. Nos. 5,539,082, 5,705, 333, and 5,773,571.

The photoactive compound has the formula where V is

Y is H, F, lower alkyl, lower alkoxy, or lower fluoroalkyl;

Z is O or S;

R, is H, R', —OR', —SR', or —NR'R" in which R' and R" independently represent H, lower alkyl, haloalkyl, alkoxy, alkylcarbonyl, or aryl, heteroaryl, or polycyclic aryl, each optionally substituted with W;

R$_2$ is aryl, heteroaryl, or polycyclic aryl, each optionally substituted with W;

B represents (1) a linear, branched, or cyclic hydrocarbon group containing from 2 to 10 carbon atoms and, if cyclic, containing a 5- or 6-membered ring or (2) a heterocyclic aromatic ring system containing a 5- or 6-membered ring, said B(1) or B(2) being substituted with 1, 2, or 3 groups of the formula R$_3$, wherein R$_3$ independently represents H, OH, NH$_2$ or COOH, or a protecting or coupling group capable of protecting or coupling a functional group during synthesis of a polynucleotide, or R$_3$ represents a nucleotide or a polynucleotide and wherein one to three carbon atoms of the hydrocarbon group can be replaced by an oxygen, nitrogen, or sulfur atom; except that B is not ribose or deoxyribose;

X represents (1) a bond, (2) a linear, branched, or cyclic hydrocarbon group containing 1 to 10 carbon atoms, in which optionally one to three carbon atoms of the hydrocarbon group are replaced by an oxygen, sulfur, or nitrogen atom wherein X is optionally substituted with 1–3 substituents selected from the group consisting of hydroxy, halogen, amino, amido, azido, carboxy, carbonyl, perfluoromethyl, and cyano functional groups; and wherein X is attached to the phenyl ring of said formula directly or through W;

n is 0, 1, 2, or 3;

each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two Ws together can represent a ring fused to the phenyl ring of said formula;

with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer.

The oxygen atom or other non-C atom (if present) of a functional group (such as an ether or carboxylate) that bridges the B-X linkage often arises from a hydroxyl group in the precursor of B, but is considered part of the X linker (for ease of defining the various groups) in this and the following formulas, unless the contrary is clear from the context of the discussion.

Within general formula I above, certain compounds are preferred. Preferred B moieties are selected from a group of first sub-formula a group of a first sub-formula a group of a second sub-formula or a group of a third sub-formula wherein $R_x$, $R_y$, and $R_z$ independently represent H or $R_3$;

m, n, p, q, and r are independently 0 or 1; and all other substituents and definitions of the formula of the compound are as previously defined for general formula I.

A hydrogen atom of the B moiety is replaced by a covalent bond to the X group, usually a hydrogen of a hydroxyl group (i.e, at least one $R_3$ would represent a hydroxyl group in, such a precursor molecule). However, this preference is for convenience of synthesis only, as the resulting B-X linkage can readily be prepared from (poly) hydroxy hydrocarbon precursors, many of which are commercially available. Other hydrogens can be replaced by the indicated covalent bond if desired. The actual molecules used in synthesis are often still derived from a (poly) hydroxy compound in which one of the hydroxyl groups has been replaced by the functional group, often through a series of reactions. For example, a hydroxyl group can be replaced by a halogen atom or other leaving group, and the leaving group can participate in bond formation with an electron donating group in the precursor of the X group.

Compounds in which B is formed from a saturated hydrocarbon are preferred, although unsaturated compounds (including cyclic aromatics) are permitted.

Compounds of formula I in which B is the third option are preferred, especially those in which m+n+p+q+r=0, 1, or 2. Even more preferably, these compounds represent an acyclic, saturated, di- or tri-hydroxy hydrocarbon, especially glycerol and 1,2- or 1,3-dihydroxyalkanes of 3 to 5 carbons that are attached to the X group at their terminal position furthest from the indicated hydroxyl groups, such as 4,5-dihydroxypentyl, 3,5-dihydroxypentyl, 2,4-dihydroxy-2-methylbutyl, 3-hydroxy-2-(hydroxymethyl)propyl, and 2,3-dihydroxypropyl.

Aromatic ring systems may be present in the B moiety. These include both hydrocarbon and hetererocyclic aromatic ring systems. Compounds in which B comprises a benzene or naphthalene ring system are preferred, especially 1,2-di (hydroxymethy)-substituted aromatics. The same substituents are preferred when B comprises a heterocyclic ring system, such as a pyran, pyrrole, pyrazole, imidazole, piperidine, pyridine, pyrazine, pyrimidine, pyrazidine, thiophene, acridine, indole, quinoline, isoquinoline, quinazoline, quinoxaline, xanthene or 1,2-benzopyran ring systems.

Also within the scope of the invention are compounds in which B comprises a bridged hydrocarbon ring system, such as bicyclo [3.1.0] hexane or [2.2.1] heptane ring system. These molecules have configurations with reduced mobility so that various cis and trans substitution pattern can be easily prepared and maintained. See, for example, Ferguson, "Organic Molecular Structure," Willard Grant, Boston, 1975, chapters 17–19, for a review of this chemistry and synthetic techniques. In a like manner, compounds in which B comprises a spiro or dispiro hydrocarbon ring system are also within the scope of the invention.

As previously noted, the X linking group is not particularly restricted in structure, as it is not present in a part of the molecule that interacts either with the remainder of the backbone structure or with a complementary strand of a polynucleotide. However, there are preferred structures for this part of the molecule, such as the following, which can represent X, in either of the two possible orientations:

in which J represents H, F, Cl, I, or Br and n=0, 1, or 2.

Other preferred compounds are those in which X comprises a cyclic structure with a 5- or 6-membered carbon or heterocyclic ring (the latter containing one O, S, or N atom), such as cyclopentane, cyclohexane, dihydrofuran, pyrrole, or pyridine.

Compounds in which W is hydrogen are preferred.

The compounds of formula I in which a nucleotide or polynucleotide is connected to the compound are usually (but not always) connected via a phosphorous-containing linking group. Preferred phosphorous-containing linking groups, as well as other linking groups, are discussed elsewhere. Such compounds are preferred compounds of the invention, as they can be used directly in the assays and crosslinking processes that are the principal end use of this invention. These compounds have the formula $(N_{m1}QN_{m2})_{m3}$ in which m1 and m2 are integers from 0 to 200, preferably 0 to 50, more preferably 0 to 30; m3 is an integer from 1 to 10, preferably 1 to 5; each N independently represents a nucleotide of a desired polynucleotide sequence; Q represents the nucleotide-replacing molecule of the invention incorporated into the normal polynucleotide sequence. Preferred lengths of uninterrupted normal nucleotide sequences are as set out above for m1 and m2.

In addition to the naturally occurring bases A, T, G, C, U there may also be contained within each desired nucleotide sequence N, synthetic nucleoside analogs, such as 5-methylcytidine, 2-aminoadenine and the like which help to stabilize nucleic acid duplexes; or inosine, nebularine, or 3-nitropyrrole and the like or a mixture of bases at one position, or a simple spacer molecule, which help to overcome polymorphisms in the target sequence when developing hybridization probes. Q can be present either in the interior of the polynucleotide or at one of its terminal positions. In an interior position, at least two $R_3$ groups must be present in order to allow the Q molecule to connect to ends of two separate strands; if Q is inserted at a terminal position, only one $R_3$ is required, although others may be present in both cases.

In these formulas it should be recognized that each $N_{m1}Q$ $N_{m2}$ can differ from each other in a polynucleotide sequence in which m3 is greater than 1; i.e., multiple Q moieties can be present randomly along the length of a molecule, provided that the remaining, parameters described above are complied with.

One group of preferred polynucleotides has a long sequence of uninterrupted normal bases with 1–5 Q moieties present at either or both ends of the molecule (preferably 1–3 Q moieties). As noted, the Q moieties can be either consecutive or can be interrupted with a few normal nucleotides. Plural Q moieties (either consecutive or not) in the middle of a probe also represents a preferred embodiment, with relatively long uninterrupted sequences to either side of the crosslinking Q units.

In all preferred embodiments, there is at least one uninterrupted sequence of nucleotides that is complementary to the corresponding target nucleotides. This uninterrupted sequence provides stability during the hybridization process so that proper factors that lead to stability and selectivity and recognition of the target will occur. The factors that lead to stability and selectivity are the same in the present process as in any other hybridization process. Uninterrupted sequences of complementary nucleotides followed by Q moieties are no different in this regard from uninterrupted sequences of target nucleotides followed by a non-complementary normal base. Thus, the stability of polynucleotides containing the crosslinking moiety of the invention can readily be predicted from standard considerations of nucleic acid hybridization.

In another preferred embodiment, the probe containing the crosslinking unit Q is comprised of a sequence of nucleotides that is complementary to a target sequence and another sequence of nucleotides within which Q is located that is not complementary to the target. This region of the probe being thus available to hybridize with a portion of another probe which is complementary to the adjacent region of the target. In one instance, two probes and a target hybridize to form a three-arm structure with the crosslinking unit Q of the probes located within the probe-probe hybrid portion of the structure. In another instance, probe and target complexes combine to form four-arm structures with the crosslinking unit Q of the probes located within a probe-probe hybrid portion of the structure.

Also preferred are compounds in which two $R_3$ groups are present in the B moiety and both represent a different hydroxyl-coupling or hydroxyl-protecting group, as such compounds are ready for use in the synthesis of a crosslinkable polynucleotide. These protecting and activating groups are also discussed elsewhere in this specification.

Another particularly preferred group of compounds of the invention have the formula II below:

where
$n_1$ is 0 to 10 (preferably 0 to 5, more preferably 1 to 3);
$n_2$ is 0 to 5 (preferably 0 to 2, more preferably 0 or 1);
$n_3$ is 0 to 5 (preferably 0 to 2, more preferably 0 or 1);

V is

Y is H, F, lower alkyl, lower alkoxy, or lower fluoroalkyl;
Z is O or S;
$R_1$ is H, —OR', —SR', or —NR'R" in which R' and R" independently represent H, lower alkyl, haloalkyl, alkoxy, alkylcarbonyl, or aryl, heteroaryl, or polycyclic aryl, each optionally substituted with W;
$R_2$ is aryl, heteroaryl or polycyclic aryl, each optionally substituted with W;
each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two Ws together can represent a ring fused to the phenyl ring of said formula;
X is an organic group containing (a) 1 to 10 carbon atoms and (b) 0 to 10, preferably 0 to 2, hetero atoms selected from the group consisting of O, S and N, and wherein X comprises a shortest linking chain of 1 to 10 atoms between the other atoms of the formula to which it is attached;
$R_3$ is H, OH, $NH_2$, COOH, or a group capable of coupling with or protecting a functional group during automated polynucleotide synthesis. Alternatively $R_3$ represents a nucleotide or polynucleotide linked to the compound by a phosphodiester linkage or other typical group used to couple monomeric units in polynucleotides. Preferred coupling groups include phosphorous containing groups such as phosphite, phosphoramidite, phosphate, H-phosphonate, triphosphate, phosphorothioate, phosphorodithioate, and methyl phosphonamidite. Non-phosphorous coupling groups include carboxy groups, carbamates, amines and amides. Typical protecting groups include trityl, dimethoxytrityl, monomethoxytrityl, pixyl, t-butoxy carbonyl (Boc), fluorenylmethoxycarbonyl (Fmoc), 6-nitroveratryl, 6'-nitropiperonyl, pyrenylmethyl, methyl-6-nitroveratryl, and methyl-6-nitropiperonyl groups.

Compounds of the invention are useful either as intermediates in the preparation of, or as components of, photoactivate polynucleotides used for example as probes in hybridization assays. Since the intention is that one or more of these molecules eventually form part of a polynucleotide, the backbone moiety that forms part of the molecules is derived either from glycerin or a different polyhydroxyl hydrocarbon molecule in most cases. The glyceryl or other polyhydroxyl hydrocarbon molecule is incorporated at any position of the backbone of a nucleic acid typically by phosphodiester type linkage with the 3' and/or 5' hydroxyl groups of the adjacent nucleotides in the molecule, with the crosslinking moiety normally being attached to the backbone moiety prior to such incorporation.

The crosslinking moiety of the compound of the invention can be derived from any number of substituted aryl olefins. An organic functional group at the position in the crosslinking moiety precursor where glycerin or another backbone moiety will be attached is typically used to join the crosslinking moiety to the backbone moiety in the final product. Since final products can be often prepared by alternative synthetic routes, any given final product will likely have several possible precursors. The linking moiety can arise from a separate molecule or be formed by reaction portions of the crosslinking moiety precursor and the backbone moiety precursor.

At locations other than the linking position, the aryl ring system can be either unsubstituted or substituted. Typical substituents on the ring are small, stable substituents normally found on aromatic rings in organic compounds. Substituents can be selected as desired to change the excitation wavelength.

In certain preferred embodiments the aryl moiety precursor, prior to reaction with the backbone moiety precursor, will have the formula:

in which $n_2$, V, and $W_n$ have the meanings previously defined; and $X_1$ is a precursor of all or part of the X linking moiety. $X_1$ will react with an organic functional group on the precursor of the linker moiety to form a covalent bond. Typical reactive functional groups include hydroxy, amine, halogen, thio, carbonyl, carboxy ester, carboxy amide, silyl and vinyl groups. These precursors can be synthesized by standard methods of organic synthesis from the many commercially available aryl derivatives.

In certain preferred embodiments the backbone moiety precursor has the formula:

in which $R_3$, $R_4$, and $n_1$, and $n_3$ have the meaning previously defined and $X_2$ is a precursor of all or part of the X linking group.

$X_2$ will react with an organic functional group on the aryl moiety to form a covalent bond in the final linking X moiety. $X_2$ typically will be selected from reactive functional groups and nucleophilic and electrophilic groups that are capable of undergoing nucleophilic or electrophilic substitution or addition. Examples of specific functional groups include hydroxy, amino, halogen, thio, carbonyl, carboxy ester, carboxy amide, vinyl, and silicon derivatives. This precursor can be synthesized by standard methods of organic synthesis from (poly)hydroxyhydrocarbons such as glycerin, commercially available 1,2- or 1,3-dihydroxyalkane derivatives, such compounds with a protected hydroxyl group at the location of the indicated hydroxyl groups, or compounds that may be converted to a (poly)hydroxyhydrocarbon in subsequent reactions, such as, for example, olefins, carbonyls, halides, or epoxides. Such reactions are typical in organic synthetic reaction schemes; more examples may be found in Larock, R. C., Comprehensive Organic Transformation: A Guide to Functional Group Preparations, VCH Publishers: New York 1989. See Misiura, K., Durrant, I., Evans, M. R., and Gait, M. J., Nucleic Acids Res. (1990) 18, 4345–4354, which is herein incorporated by reference, for a discussion of attaching moieties having structures similar to those of the present backbone moieties to bases used in polynucleotide synthesis.

Compounds of the invention can be prepared by standard techniques of synthetic organic chemistry, using the guidelines outlined in this specification. For example, a typical synthesis based on commercially available starting materials is set forth in the following Examples.

Example 1

Synthesis of a Crosslinker Based on Benzylideneacetone

Compound 1

Figure 1:
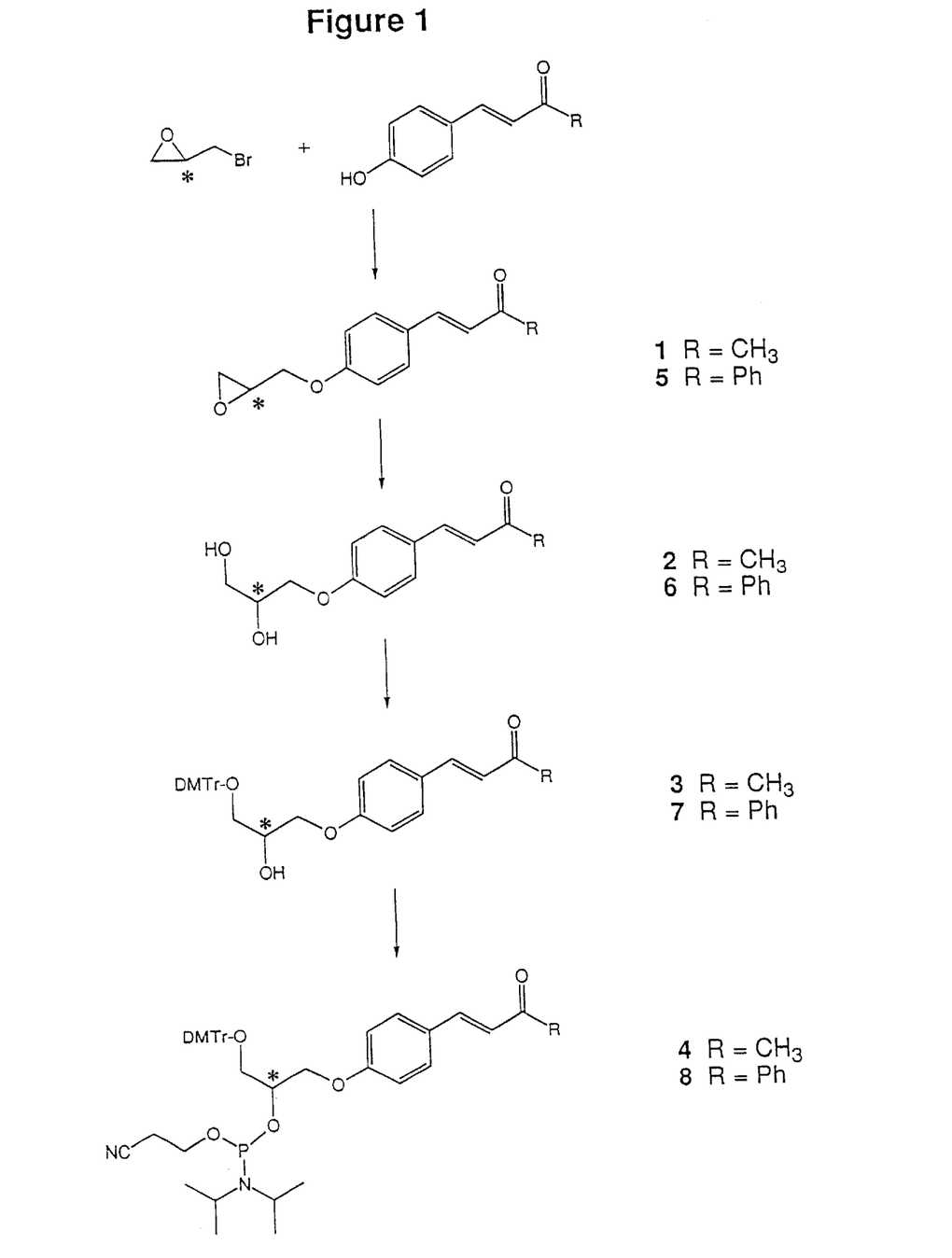
FIG. 1 is a flow chart illustrating the synthetic pathway to compounds 4 and 8, which is described in Examples 1 and 2, below. DMTr represents 4,4'-dimethoxytrityl.

4-(4'-Hydroxyphenyl)-3-buten-2-one [4-hydroxybenzylideneacetone] (590 mg, 3.6 mmol), epibromohydrin (0.26 mL, 3.04 mmol) and potassium carbonate (490 mg, 3.5 mmol) were combined in acetone (10 mL) and the mixture was refluxed for 4 h. Dimethylformamide (5 mL) was added, and the mixture was refluxed for 1 h. The reaction mixture was diluted with 10% NaOH solution and extracted with ethyl acetate. The organic phase was dried over $Na_2SO_4$, and the solvent was removed by rotary evaporation. A yellow crystalline material was obtained in 90% yield (600 mg).

Compound 2

A solution of 1 (600 mg, 2.75 mmol) and sulfuric acid (0.8 mL of 2 M solution) in acetone (3 mL) was heated to 50° C. for 30 min. The solution was diluted with aqueous NaCl (saturated) and then extracted with ethyl acetate. The organic solution was dried over $Na_2SO_4$ and the solvent was removed by rotary evaporation. TLC indicated the starting material was completely converted to a compound with lower $R_f$. A yellow solid was obtained in 97% yield (630 mg).

Compound 3

A solution of the diol 2 (630 mg, 2.67 mmol), 4,4'-dimethoxytrityl chloride (995 mg, 2.94 mmol), 4-(dimethylamino)pyridine (31 mg, 0.25 mmol) and triethylamine (0.37 mL, 2.67 mmol) in pyridine (12 mL) was stirred at room temperature for 1 hr. The reaction solution was diluted with ethyl acetate (20 mL) and extracted three times with water (15 mL). The organic fraction was dried over $Na_2SO_4$ and the solvent was removed by rotary evaporation. The crude product was chromatographed on silica gel, eluted with hexane/acetone/triethylamine (74:24:2, v/v/v). The appropriate fractions were collected and combined to provide 3 in 33% yield (500 mg).

Compound 4

The DMT derivative 3 (500 mg, 0.9 mmol) and triethylamine (0.4 mL, 2.87 mmol) were added to dry methylene chloride (4 mL) under an argon atmosphere. To this rapidly stirred solution 2-cyanoethyl diisopropylchlorophosphoramidite (0.35 mL, 1.5 mmol) was added dropwise. The solution was stirred at room temperature for 30 min. The solution was diluted with water, then extracted with triethylamine/ethyl acetate (1:49, v/v). The organic phase was dried over $Na_2SO_4$ and the solvent was removed by rotary evaporation. The viscous oil was chromatographed on silica gel, eluted with hexane/acetone/triethylamine (79:19:2, v/v/v). The appropriate fractions were collected and combined to provide 4 in 75% yield (500 mg).

Example 2

Synthesis of a Crosslinker Based on Benzylidenephenone

Compound 5

1-Phenyl-3-(4'-hydroxyphenyl)-2-propen-1-one [4-hydroxybenzylidenephenone] (1.10 g, 3.6 mmol), epibromohydrin (0.5 mL, 5.84 mmol) and potassium carbonate (840 mg, 6.1 mmol) were combined in acetone (20 mL) and the mixture was refluxed for 18 h. The solvent was removed by rotary evaporation, the residue was dissolved in ethyl acetate and extracted with 2N aqueous sodium hydroxide. The organic phase was dried over $Na_2SO_4$, and the solvent was removed by rotary evaporation. The crude product was obtained as an oil in 95% yield (1.3 g).

Compound 6

A solution of 5 (680 mg, 2.43 mmol) and 2 M sulfuric acid (1.0 mL) in acetone (6 mL) was heated to 60° C. for 30 min. The same procedure used to prepare 2 was followed, to provide 6 in 74% yield (540 mg).

Compound 7

A solution of the diol 6 (540 mg, 1.81 mmol), 4,4'-dimethoxytrityl chloride (680 mg, 2.01 mmol), 4-(dimethylamino)pyridine (20 mg, 0.16 mmol) and triethylamine (0.25 mL, 1.8 mmol) in pyridine (9 mL) was stirred at room temperature for 1 hr. The same procedure used to prepare 3 was followed, to provide 7 in 58% yield (630 mg).

Compound 8

Under an argon atmosphere, to a rapidly stirred solution of the DMT derivative 7 (620 mg, 1.03 mmol) and N,N-diisopropylethylamine (0.3 mL, 1.72 mmol) in dry methylene chloride (2 mL) was added 2-cyanoethyl diisopropylchlorophosphoramidite (0.4 mL, 1.8 mmol). The same procedure used to prepare 4 was followed, to provide 8 in 48% yield (400 mg).

Example 3

Synthesis of a Crosslinker Based on 4-Methoxybenzylidenephenone

Compound 9

Figure 2:
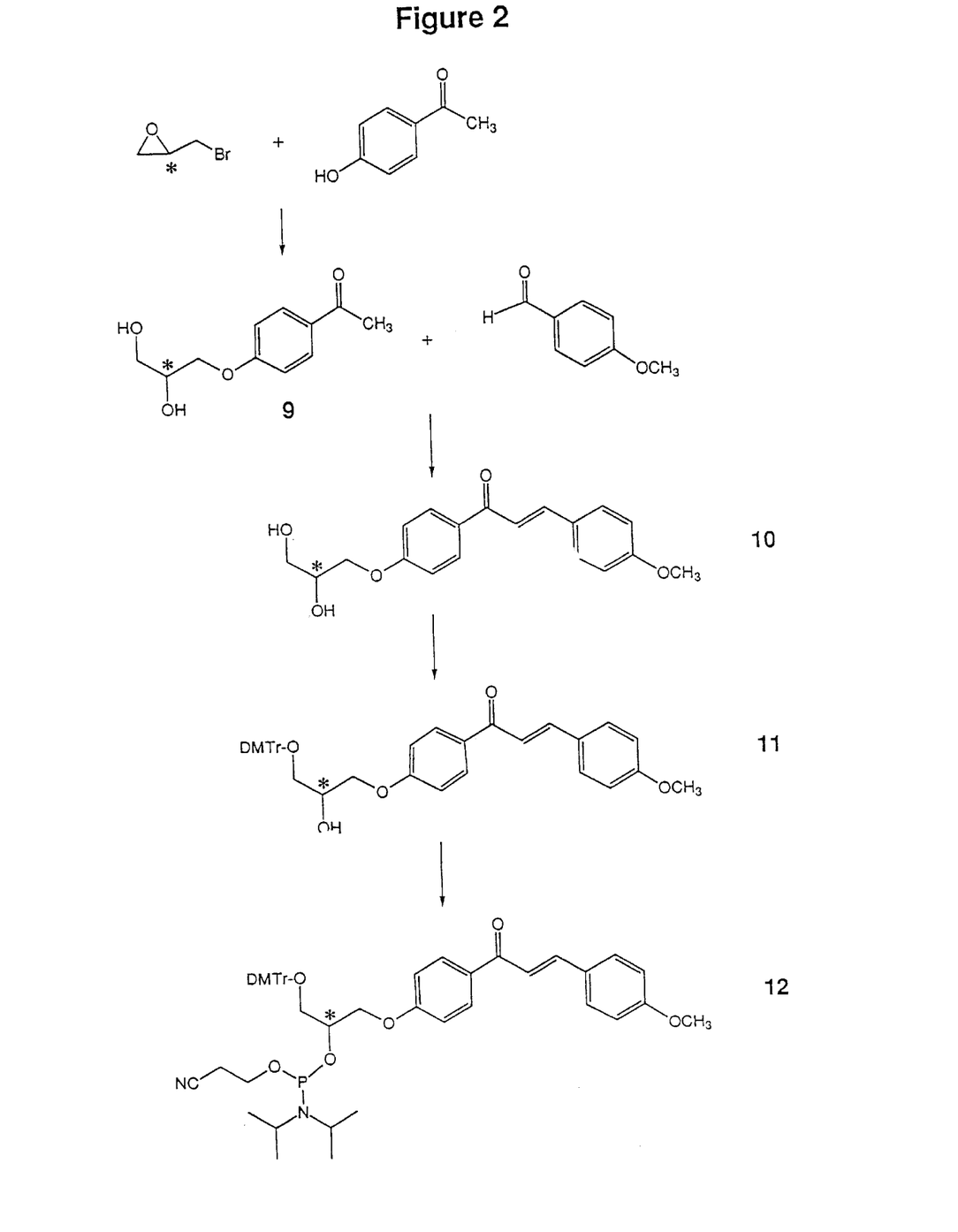
FIG. 2 is a flow chart illustrating the synthetic pathway to compound 12, which is described in Example 3, below. DMTr represents 4,4'-dimethoxytrityl.

4'-Hydroxyacetophenone (6.80 g, 49.9 mmol), epibromohydrin (4.5 mL, 52.6 mmol) and potassium carbonate (7.0 g, 50.6 mmol) were combined in acetone/dimethylformamide (15 mL/5 mL) and the mixture was refluxed for 2 h. The solvent was removed by rotary evaporation, the residue was dissolved in ethyl acetate and extracted with 2N aqueous sodium hydroxide. The organic phase was dried over $Na_2SO_4$, and the solvent was removed by rotary evaporation. The crude product (8.0 g) was combined with 2 M sulfuric acid (4 mL) in acetone (10 mL) and was heated to 60° C. for 30 min. The reaction solution was diluted with aqueous NaCl (saturated) and then extracted with ethyl acetate. The organic solution was dried over $Na_2SO_4$ and the solvent was removed by rotary evaporation. The crude product was chromatographed on silica gel, eluted with 30% (v/v) acetone/hexane. The appropriate fractions were collected and combined to provide 9 in 20% yield (2.0 g).

Compound 10

According to a literature procedure (*Org. Syn. Coll.* 1, 78) an alkaline aqueous ethanol solution was prepared with 270 mg sodium hydroxide dissolved in water (1 mL) and ethanol (3 mL) and chilled in an ice/water bath. The diol 9 (1.2 g, 6 mmol) was dissolved in ethanol (6 mL) and added dropwise while stirring the chilled aqueous ethanol solution. After addition was complete, anisaldehyde (0.81 g, 6 mmol) was added at once and the temperature of the reaction mixture maintained between 15°–30° C. After 2 h the solid was collected on a Buchner funnel and washed with water until the washings were neutral. The solid was finally washed with chilled 50% (v/v) ethanol/acetone. After drying, 10 was obtained in 31% yield (620 mg).

Compound 11

A solution of the diol 10 (600 mg, 1.83 mmol), 4,4'-dimethoxytrityl chloride (1.5 g, 4.43 mmol), 4-(dimethylamino)pyridine (53 mg, 0.44 mmol) and triethylamine (0.6 mL, 4.3 mmol) in pyridine (10 mL) was stirred at room temperature for 1 hr. The same procedure used to prepare 3 was followed, to provide 11 in 29% yield (340 mg).

Compound 12

Under an argon atmosphere, to a rapidly stirred solution of the DMT derivative 11 (230 mg, 0.36 mmol) and N,N-diisopropylethylamine (0.125 mL, 0.72 mmol) in dry methylene chloride (1.5 mL) was added 2-cyanoethyldiisopropylchlorophosphoramidite (0.2 mL, 0.9 mmol). The same procedure used to prepare 4 was followed, to provide 12 in 50% yield (150 mg).

Example 4

Synthesis of Probes with Crosslinkers

Synthetic oligonucleotide probes were prepared according to the β-cyanoethylphosphor-amidite method on an automated DNA synthesis instrument (Millipore, Expedite 8909). Crosslinking compounds were incorporating by preparing diols with one hydroxy group activated as a phosphoramidite derivative and one hydroxy group protected as a dimethoxytrityl derivative. The protected/activated compound was dissolved in dry acetonitrile (concentration 50–100 mM) in a reagent bottle and placed on an extra port on the automated instrument. Oligonucleotides were prepared on a 0.2 μmol scale using the standard instrument protocols. Following automated synthesis, the oligonucleotides were cleaved from the solid support and deprotected by treatment with concentrated ammonium hydroxide at 55° C. for 30 minutes. The ammonia was removed in vacuo, the aqueous solution was extracted with butanol, and the oligonucleotide purified by denaturing polyacrylamide gel electrophoresis. The band of the desired oligonucleotide was excised from the gel and eluted into water. Gel purified oligonucleotides were desalted by Sep-Pak C18 (Waters Corp.) treatment according to the manufacturer's procedure.

Example 5

Crosslinking Reactions in a Duplex

Sequences

Probe 1: 5'-AXA GCG CGC AAA GAC AAA AT (SEQ ID NO: 1)
Probe 2: 5'-ATT TTG TCT TTG CGC GCT TT (SEQ ID NO: 2)
Probe 3: 5'-AZA GCG CGC AAA GAC AAA AT (SEQ ID NO: 3)
Probe 4: 5'-ATT TTG TCT TTG CGC GCT ZT (SEQ ID NO: 4)

where X is the non-nucleosidic coumarin derivative disclosed in Wood et al. (PCT Appl. Publication Number WO96/28438) based on 3-O-(7-coumarinyl) glycerol, and Z is based on the chalcone derivative described in Example 2. The oligonucleotides were prepared according the procedures of Example 4.

Probes 2 and 4 were 5'-end labeled with $^{32}$P phosphate using polynucleotide kinase and $\gamma$-$^{32}$P-ATP according to standard procedures.

Complementary pairs of probes were tested for crosslinking rates in the following combinations: 1 and 2, 3 and 2, 3 and 4. The unlabeled probe (1 or 3) was present in 10-fold molar excess over the labeled probe (2 or 4).

Five identical samples of each of the probe combinations were prepared and then separately irradiated for times ranging from 1 to 60 minutes. The probes were hybridized in buffer for 20 minutes at 40° C., and then irradiated with UV-A light in an irradiation chamber (UV Products, CL-1000) for the specified length of time.

The hybridization buffer was composed of bovine serum albumin, 0.1225%; sodium acetate, 68 mM; SSC (saline sodium citrate) 4.515×; and TE (Tris EDTA) 0.28×. The sample volume was 90 µL, and contained 0.5 pmol of labeled probe and 5.0 pmol of unlabeled probe.

The extent of crosslinking as a function of time was determined by separating the crosslinked and non-crosslinked probes by denaturing polyacrylamide gel electrophoresis, followed by quantifying the amount of radiolabeled probe in each band by scintillation counting of the excised bands.

Results:

% Crosslinking as a Function of Irradiation Time

|  | Irradiation Time [minutes] | | | | |
| --- | --- | --- | --- | --- | --- |
| Probe Set | 1 | 3 | 9 | 27 | 60 |
| Probe 1 & 2 | 12 | 29 | 63 | 86 | 93 |
| Probe 3 & 2 | 1.2 | 1.4 | 2.9 | 5.7 | 9.5 |
| Probe 3 & 4 | 83 | 84 | 84 | 83 | 83 |

The results indicate that the crosslinking compound Z disclosed herein, found in probes 3 and 4, react very rapidly to provide crosslinked strands of oligonucleotides. In contrast, the reaction between crosslinker Z and a probe that only contains natural bases (probes 3 and 2) is relatively slow, and the extent of reaction can be considered negligible at short times: 83% vs. 1.2% with 1 minute of irradiation. The crosslinking compound X disclosed previously attains greater than 86% conversion to the crosslinked product with 30–60 minutes of irradiation, though this is achieved via a steady increase in the amount of product over the initial 30 minutes of irradiation. In contrast, the crosslinker Z has achieved the full extent of reaction by the first minute, providing a substantial increase in the time efficiency of the crosslinking process.

Example 6

Crosslinking Reactions in a Three-Armed Structure

Sequences

Probe 5: 5'-TCT AGG TTC ATG ACA AGC TCG TCA GAX A (SEQ ID NO:5)
Probe 6: 5'-TTT TTT CCT CAA GAG CAT TGT AAG CAG AAG ACT T (SEQ ID NO:6)
Probe 7: 5'-TCT AGG TTC ATG ACA AGC TCG TCA GAZ A (SEQ ID NO: 7)
Probe 8: 5'-TTT TZT CCT CAA GAG CAT TGT AAG CAG AAG ACT T (SEQ ID NO: 8)
Probe 9: 5'-TAA GTC TTC TGC TTA CAA TGC TCT TGA GGC TGA CGA GCT TGT CAT GAA CCT AGA T (SEQ ID NO: 9)

where X is the non-nucleosidic coumarin derivative disclosed in Wood et al. (PCT Appl. Publication Number WO96/28438) based on 3-O-(7-coumarinyl) glycerol, and Z is based on the chalcone derivative described in Example 2. The oligonucleotides were prepared according the procedures of Example 4.

Probes 6 and 8 were 5'-end labeled with $^{32}$P phosphate using polynucleotide kinase and $\gamma$-$^{32}$P-ATP according to standard procedures.

The general procedure was the same as that for Example 5. Four replicates of each sample were prepared, and each sample contained 0.5 pmol of the labeled probe and 5.0 pmol of the unlabeled probes.

Results:

% Crosslinking as a Function of Irradiation Time

|  | Irradiation Time [minutes] | | | |
| --- | --- | --- | --- | --- |
| Probe Set | 1 | 4 | 16 | 60 |
| Probe 5 & 6 & 9 | 28 | 67 | 85 | 86 |
| Probe 7 & 6 & 9 | 1.7 | 2.9 | 7.1 | 16 |
| Probe 7 & 8 & 9 | 51 | 55 | 59 | 58 |

The results indicate that the crosslinking compound Z disclosed herein, found in probes 7 and 8, react very rapidly to provide crosslinked strands of oligonucleotides. In contrast, the reaction between crosslinker Z and a probe that only contains natural bases (probes 7 and 6) is relatively slow, and the extent of reaction can be considered negligible at short times: 51% vs. 1.7% with 1 minute of irradiation. The crosslinking compound X disclosed previously attains greater than 85% conversion to the crosslinked product with 16–60 minutes of irradiation, though this is achieved via a steady increase in the amount of product over the initial 16 minutes of irradiation. In contrast, the crosslinker Z has nearly achieved the full extent of reaction by the first minute, providing a substantial increase in the time efficiency of the crosslinking process.

Example 7

Crosslinking Reactions in a Three-Armed Structure Between Different Crosslinking Agents Sequences Probe 10: 5'-TCT AGG TTC ATG ACA AGC TCG TCA GAX A (SEQ ID NO: 10)

Probe 11: 5'-TCT AGG TTC ATG ACA AGC TCG TCA GAZ A (SEQ ID NO: 11)

where X is the R enantiomer of the non-nucleosidic coumarin derivative disclosed in Wood et al. (PCT Appl. Publication Number WO96/28438) based on 3-O-(7-coumarinyl) glycerol, and Z is based on the chalcone derivative described in Example 1. The oligonucleotides were prepared according the procedures of Example 4.

Probe 8, containing the chalcone derivative described in Example 2 was 5'-end labeled with $^{32}$P phosphate using polynucleotide kinase and $\gamma$-$^{32}$P-ATP according to standard procedures.

The general procedure was the same as that for Example 5. Four replicates of each sample were prepared, and each sample contained 0.5 pmol of the labeled probe and 5.0 pmol of the unlabeled probes.

Results:

% Crosslinking as a Function of Irradiation Time

|  | Irradiation Time [minutes] | | | |
| --- | --- | --- | --- | --- |
| Probe Set | 1 | 4 | 16 | 60 |
| Probe 10 & 8 & 9 | 18 | 47 | 71 | 82 |
| Probe 11 & 8 & 9 | 28 | 33 | 36 | 41 |

The results indicate that the crosslinking compounds disclosed herein, found in probes 8 and 11, and another photoactive compound known to undergo 2+2 photocyclization reactions, found in probe 10, crossreact very rapidly to provide crosslinked complexes of oligonucleotides.

It will be apparent to one of ordinary skill in the art that many changes and modifications can be made to the invention without departing from the spirit or scope of the appended claims.

All publications and patent applications mentioned in this specification are herein incorporated by reference.

What is claimed is:

1. A compound of the formula:

where V is

Y is H, F, lower alkyl, lower alkoxy, or lower fluoroalkyl;

Z is O or S;

$R_1$ is H, R'—OR', —SR', or —NR'R" in which R' and R" independently represent H, lower alkyl, haloalkyl, alkoxy, alkylcarbonyl, or aryl, heteroaryl, or polycyclic aryl, each optionally substituted with W, except that $R_1$ is not OH when V is YC=CY—C(Z)—$R_1$;

$R_2$ is aryl, heteroaryl or polycyclic aryl, each optionally substituted with W;

B represents (1) a linear, branched, or cyclic hydrocarbon group containing from 2 to 10 carbon atoms and, if cyclic, containing a 5- or 6-membered ring or (2) a heterocyclic aromatic ring system containing a 5- or 6-membered ring, said B(1) or B(2) being substituted with 1, 2, or 3 group of the formula $R_3$, wherein $R_3$ independently represents H, OH, $NH_2$ or COOH or a protecting or coupling group capable of protecting or coupling a functional group during synthesis of a polynucleotide, or $R_3$ represents a nucleotide or a polynucleotide connected to the remainder of said formula, and wherein one to three carbon atoms of the hydrocarbon group can be replaced by an oxygen, nitrogen, or sulfur atom; except that B is not ribose or deoxyribose;

X represents (1) a bond, (2) a linear, branched, or cyclic hydrocarbon group containing 1 to 10 carbon atoms, in which optionally one to three carbon atoms of the hydrocarbon group are replaced by an oxygen, sulfur, or nitrogen atom wherein X is optionally substituted with 1–3 substituents selected from the group consisting of hydroxy, halogen, amino, amido, azido, carboxy, carbonyl, perfluoromethyl, and cyano functional groups; and wherein X is attached to the phenyl ring of said formula directly or through W;

n is 0, 1, 2, or 3;

each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two W's together can represent a ring fused to the phenyl ring of said formula;

with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer.

2. The compound of claim 1, wherein X, in either orientation, is in which J represents H, F, Cl, I, or Br and n=0, 1, or 2.

3. The compound of claim 1, wherein X is a cyclic structure with a 5- or 6-membered ring or a 5- or 6-membered heterocycle containing at least one O, S, or N atom.

4. The compound of claim 1, wherein V is

5. The compound of claim 1, wherein V is

6. The compound of claim 1, wherein V is

7. The compound of claim 1, wherein X is oriented meta or para to the olefin.

8. The compound of claim 1, wherein B represents:
a group of a first sub-formula a group of a second sub-formula or a group of a third sub-formula wherein $R_x$, $R_y$, and $R_z$ independently represent H or $R_3$;

m, n, p, q, and r independently represent 0 or 1; and one hydrogen of said sub-formulas is replaced by a covalent bond to said X group.

9. The compound of claim 1, wherein B is saturated.

10. The compound of claim 8, wherein B has said third sub-formula.

11. The compound of claim 10, wherein m+n+p+q+r=0, 1, or 2.

12. The compound of claim 8, wherein said third sub-formula represents an acyclic, saturated, di- or tri-hydroxyhydrocarbon.

13. The compound of claim 8 wherein said third sub-formula represents tri-O-substituted glycerin.

14. The compound of claim 1, wherein said nucleotide or polynucleotide is connected to said compound via a phosphorous-containing linking group.

15. The compound of claim 14 wherein said phosphorous-containing group is a phosphodiester group.

16. The compound of claim 1, wherein B comprises a benzene or naphthalene ring.

17. The compound of claim 1, wherein B contains a bridged hydrocarbon ring.

18. The compound of claim 1, wherein B contains a bicyclo [3.1.0] hexane or [2.2.1] heptane ring.

19. The compound of claim 1, wherein B contains a spiro or dispiro hydrocarbon ring.

20. The compound of claim 1, wherein at least one $R_3$ is selected from the group consisting of phosphite, phosphoramidite, phosphate, H-phosphonate, triphosphate, phosphorothioate, phosphorodithioate, and methyl phosphonamidite.

21. The compound of claim 1, wherein B contains a heterocyclic ring selected from the group consisting of pyran, pyrrole, pyrazole, imidazole, piperidine, pyridine, pyrazine, pyrimidine, pyridazine, thiophene, acridine, indole, quinoline, isoquinoline, quinazoline, quinoxaline, xanthene, and 1,2-benzopyran.

22. A polynucleotide of the formula $(N_{m1}QN_{m2})_{m3}$ in which each N represents a nucleotide of a desired polynucleotide sequence, Q represents a molecule of claim 1, and each m1, m2, and m3 are integers, and m3 is from 1 to 10 wherein each (NQN) group may have different values of m1, m2, and m3.

23. A compound of claim 22 wherein m1 and m2 are less than 100.

24. A compound of claim 22 wherein at least one Q is at a terminal position and at least one Q is at an interior position of said polynucleotide sequence.

25. A compound of claim 22 wherein at least one Q is at a interior position of said polynucleotide sequence.

26. A compound of claim 22 wherein Q is at a terminal position of said polynucleotide sequence.

27. A compound of claim 1 wherein B—X— is $R_3$—O—$CH_2$—$CH_2$—O—$CH_2$—$CH_2$—O—$CH_2$—$CH(OR_3)$—$CH_2$—O—.

28. An optically active compound of claim 1 in the R or S configuration or a racemic mixture thereof.

29. A nucleic acid probe comprising at least one compound of claim 1.

30. A complex comprising a probe of claim 29 crosslinked to a target oligonucleotide.

31. A complex comprising two probes of claim 29 wherein each of said probes contains a different photoactive compound.

32. A complex comprising two probes of claim 29 wherein each of said probes contains the same photoactive compound.

33. A compound of the formula:

where V is

Y is H, F, lower alkyl, lower alkoxy, or lower fluoroalkyl;

Z is O or S;

$R_1$ is H, R'—OR', —SR', or —NR'R" in which R' and R" independently represent H, lower alkyl, haloalkyl, alkoxy, alkylcarbonyl, or aryl, heteroaryl, or polycyclic aryl, each optionally substituted with W;

$R_2$ is aryl, heteroaryl or polycyclic aryl, each optionally substituted with W;

X represents (1) a bond, (2) a linear, branched, or cyclic hydrocarbon group containing 1 to 10 carbon atoms, in which optionally one to three carbon atoms of the hydrocarbon group are replaced by an oxygen, sulfur, or nitrogen atom wherein X is optionally substituted with 1–3 substituents selected from the group consisting of hydroxy, halogen, amino, amido, azido, carboxy, carbonyl, perfluoromethyl, and cyano functional groups; and wherein X is attached to the phenyl ring of said formula directly or through W;

n is 0, 1, 2, or 3;

each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two W's together can represent a ring fused to the phenyl ring of said formula;

with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer;

$R_3$ independently represents H, OH, $NH_2$ or COOH or a protecting or coupling group capable of protecting or coupling a functional group during synthesis of a polynucleotide, or $R_3$ represents a nucleotide or a polynucleotide, and wherein one to three carbon atoms of the hydrocarbon group can be replaced by an oxygen, nitrogen, or sulfur atom;

n1, n2, n3 are independently 0, 1, 2, or 3.

34. A nucleic acid probe comprising at least one compound of claim 33.

35. A complex comprising a probe of claim 34 crosslinked to a target oligonucleotide.

36. A complex comprising two probes of claim 34 wherein each of said probes contains a different photoactive compound.

37. A complex comprising two probes of claim 34 wherein each of said probes contains the same photoactive compound.

* * * * *

US006303799C1

(12) EX PARTE REEXAMINATION CERTIFICATE (5610th)
United States Patent
Cheng et al.

(10) Number: US 6,303,799 C1
(45) Certificate Issued: Nov. 21, 2006

(54) POLYNUCLEOTIDE CROSSLINKING AGENTS

(75) Inventors: Peter C. Cheng, San Jose, CA (US); David Albagli, Menlo Park, CA (US); Michael L. Wood, Mountain View, CA (US)

(73) Assignee: Naxcor, Menlo Park, CA (US)

Reexamination Request:
No. 90/006,829, Oct. 24, 2003

Reexamination Certificate for:
| Patent No.: | 6,303,799 |
| Issued: | Oct. 16, 2001 |
| Appl. No.: | 09/189,294 |
| Filed: | Nov. 10, 1998 |

(51) Int. Cl.
| C07D 317/44 | (2006.01) |
| C07D 307/78 | (2006.01) |
| C07D 277/22 | (2006.01) |
| C07H 19/00 | (2006.01) |
| C07H 21/04 | (2006.01) |

(52) U.S. Cl. .................. 549/441; 435/6; 435/91.1; 536/22.1; 536/23.1; 536/25.3; 536/24.3; 549/467; 548/203; 548/495; 558/254

(58) Field of Classification Search .............. None
See application file for complete search history.

(56) References Cited

U.S. PATENT DOCUMENTS

| 2,676,978 A | 4/1954 | Schmidt et al. | 260/470 |
| 2,683,171 A | 7/1954 | Schmidt et al. | 260/552 |
| 2,768,970 A | 10/1956 | Schmidt et al. | 260/552 |
| 6,004,513 A | 12/1999 | Albagli et al. | 422/68.1 |
| 6,005,093 A | 12/1999 | Wood et al. | 536/24.3 |
| 6,177,243 B1 | 1/2001 | Albagli et al. | 435/6 |
| 6,187,532 B1 | 2/2001 | Wood et al. | 435/6 |
| 6,277,570 B1 | 8/2001 | Wood et al. | 435/6 |
| 6,495,676 B1 | 12/2002 | Wood et al. | 536/25.3 |
| 6,573,048 B1 | 6/2003 | VanAtta et al. | 435/6 |
| 6,590,091 B1 | 7/2003 | Albagli et al. | 536/24.3 |
| 2001/0012616 A1 | 8/2001 | Wood et al. | 435/6 |
| 2003/0039961 A1 | 2/2003 | Albagli et al. | 435/6 |
| 2003/0134274 A1 | 7/2003 | Wood et al. | 435/5 |

FOREIGN PATENT DOCUMENTS

| DE | 0845196 | 6/1952 |
| WO | 9628438 | 9/1996 |
| WO | 9716567 | 5/1997 |
| WO | 0014281 | 3/2000 |
| WO | 0027860 | 5/2000 |
| WO | 0179563 | 10/2001 |

OTHER PUBLICATIONS

Abe et al (Yukagaku (1977), pp. 1–9 (translation of vol. 25, No. 9, pp. 30–34)).*
Albagli et al. "Chemical Amplification (CHAMP) By A Continuous, Self–Replicating Oligonucleotide–Based System" *Journal of the American Chemical Society* 121(29): 6954–6955 (1999).
Huan et al. "Photo–Cross–Linkable Oligonucleotide Probes For In Situ Hybridization Assays" *BioTechniques* 28(2):254–260 (2000).
Hwang et al. "Comparison Of The Nucleic Acid–Based Crosslinking Hybridization Assay and The Branched DNA Signal Amplification Assay In The Quantitative Measurement Of Serum Hepatitis B Virus DNA" *Journal of Clinical Laboratory Analysis* 13:296–300 (1999).
Kao et al. "Comparison Of Two Methods For Quantification Of Hepatitis B Viral DNA" *Journal of Gastroenterology and Hepatology* (14)423–426 (1999).
Lai et al. "Nucleic Acid–Based Cross–Linking Assay For Detection And Quantification Of Hepatitis B Virus DNA" *Journal of Clinical Microbiology* 37(1):161–164 (1999).
Wood et al. "Nucleic Acid Crosslinking Probes For DNA/RNA Diagnostics" *Clinical Chemistry* 42(S6): S196 (1996).
Wylenzek et al. "Evaluation Of A Nucleic Acid–Based Cross–Linking Assay To Screen for Hereditary Hemochromatosis In Healthy Blood Donors" *Clinical Chemistry* 46(11):1853–1855 (2000).
"8776. Stilonium Iodine," *The Merck Index* 11th Ed. Rahway, New Jersey: Merck and Co., Inc. (1989) pp. 8781.
Certified English Translation of DE 845 196 C, "Method to Prepare Thiosemicarbazones".
Cushman et al., "Synthesis and Evaluation of Stilbene and Dihydrostilbene derivatives as Potential Anticancer Agents that Inhibit Tubulin Polymerization," *J. Med. Chem.* 34: 2579–2588 (1991).
Francis et al., "Highly Selective Adenosine $A_2$ receptor Agonists in a Series of N–Alkylated 2–Aminoadenosines," *J. Med. Chem.* 34: 2570–2579 (1991).
Fujiwara et al., "Aromatic Substitution of Olefins. 25.[1] Reactivity of Benzene, Naphthalene, Ferrocene, and Furan Toward Styrene, and the Substituent Effect on the Reaction of Monosubstituted Benzenes with Styrene," *J. Org. Chem.* 41(10): 1681–1683 (1976).
Lutz et al., "Antimalarials. $\alpha,\beta$–Dimorpholinyl Ketones and Related Compounds," *Journal of Organic Chemistry* 14(14): 982–1000 (1949).
Rastogi, S.N. and N. Anand, "Agents Acting on the Central Nervous System. 14. 1–(p–Alkanoylphenoxy)–3–($N_4$–arylpiperazinyl)propan–2–ols. A New Class of Antidepressants," *Journal of Medicinal Chemistry* 15(3): 286–291 (1972).
Schraufstatter, E., "Die polarographische Untersuchung von Chalkonen und Flavanonen," *Experientia* 4: 192–193 (1948) [English summary on last page of article].
Schraufstatter, E., "Die bakteriostatische Wirkung von Chalkon Flavanon, Flavon und Flavonol," *Experientia* 4: 484–485 (1948) [English summary on last page of article].

* cited by examiner

*Primary Examiner*—Jeffrey Fredman (57) ABSTRACT

Novel aryl derivatives comprising an aryl olefin moiety linked to a non-nucleosidic backbone moiety are disclosed. The resulting molecules are typically used as photoactivated crosslinking groups when incorporated into oligonucleotides to crosslink nucleic acid strands.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 33 are determined to be patentable as amended.

Claims 2–32 and 34–37, dependent on an amended claim, are determined to be patentable.

1. A compound of the formula:

where V is

Y is H, F, lower alkyl, lower alkoxy, or lower fluoroalkyl;
Z is O or S;
$R_1$ is H, R', —OR', —SR', or —NR'R" in which R' and R" independently represent H, lower alkyl, haloalkyl, alkoxy, alkylcarbonyl, or aryl, heteroaryl, or polycyclic aryl, each optionally substituted with W, except that $R_1$ is not OH when V is YC=CY—C(Z)—$R_1$;
$R_2$ is aryl, heteroaryl or polycyclic aryl, each optionally substituted with W;
B represents (1) a linear, branched, or cyclic hydrocarbon group containing from 2 to 10 carbon atoms and, if cyclic, containing a 5- or 6-membered ring or (2) a heterocyclic aromatic ring system containing a 5- or 6-membered ring, said B(1) or B(2) being substituted with 1, 2, or 3 group of the formula $R_3$, wherein $R_3$ independently represents [H,] OH, $NH_2$ or COOH or a protecting or coupling group capable of protecting or coupling a functional group during synthesis of a polynucleotide, or $R_3$ represents a nucleotide or a polynucleotide connected to the remainder of said formula, and wherein one to three carbon atoms of the hydrocarbon group can be replaced by an oxygen, nitrogen, or sulfur atom; *except that B is not ribose or deoxyribose*;
X represents (1) a bond, (2) a linear, branched, or cyclic hydrocarbon group containing 1 to 10 carbon atoms, in which optionally one to three carbon atoms of the hydrocarbon group are replaced by an oxygen, sulfur, or nitrogen atom wherein X is optionally substituted with 1–3 substituents selected from the group consisting of hydroxy, halogen, amino, amido, azido, carboxy, carbonyl, perfluoromethyl, and cyano functional groups; and wherein X is attached to the phenyl ring of said formula directly or through W;
n is 0, 1, 2, or 3;
each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two W's together can represent a ring fused to the phenyl ring of said formula;
with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer.

33. A compound of the formula:

where V is

Y is H, F, lower alkyl, lower alkoxy, or lower fluoroalkyl;
Z is O or S;
$R_1$ is H, R', —OR', —SR', or —NR'R" in which R' and R" independently represent H, lower alkyl, haloalkyl, alkoxy, alkylcarbonyl, or aryl, heteroaryl, or polycyclic aryl, each optionally substituted with W;
$R_2$ is aryl, heteroaryl or polycyclic aryl, each optionally substituted with W;
X represents (1) a bond, (2) a linear, branched, or cyclic hydrocarbon group containing 1 to 10 carbon atoms, in which optionally one to three carbon atoms of the hydrocarbon group are replaced by an oxygen, sulfur, or nitrogen atom wherein X is optionally substituted with 1–3 substituents selected from the group consisting of hydroxy, halogen, amino, amido, azido, carboxy, carbonyl, perfluoromethyl, and cyano functional groups; and wherein X is attached to the phenyl ring of said formula directly or through W;
n is 0, 1, 2, or 3;
each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms; or said hydrocarbyl group substituted with 1–3 of said functional groups or in which one carbon atoms replaced by an oxygen, sulfur, or nitrogen atom and wherein two W's together can represent a ring fused to the phenyl ring of said formula;

with the provisos that (1) when X or W is a substituted hydrocarbon, the total number of substituents in X or W is less than the total number of carbon atoms in said X or W and no more than one substituent or heteroatom is attached to a given carbon, unless said substituents are halogen atoms on said given carbon, and (2) the total carbon atoms in all W substituents is 15 or fewer;

$R_3$ independently represents H, OH, $NH_2$ or COOH or a protecting or coupling group capable of protecting or coupling a functional group during synthesis of a polynucleotide, or $R_3$ represents a nucleotide or a polynucleotide, and wherein one to three carbon atoms of the hydrocarbon group can be replaced by an oxygen, nitrogen, or sulfur atom; *and* n1, n2, *and* n3 are independently 0, 1, 2, or 3.

\* \* \* \* \*

SEQUENCE LISTING

```
<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: coumarin derivative based on 3-O-(7-coumarinyl)-glycerol
      between position 1 and 2
<221> NAME/KEY: source
<222> LOCATION: (1)..(19)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 1
aagcgcgcaa agacaaaat                                           19

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: 5' end labeled with 32P phosphate
<221> NAME/KEY: source
<222> LOCATION: (1)..(20)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 2
attttgtctt tgcgcgcttt                                          20

<210> SEQ ID NO 3
<211> LENGTH: 19
<212> TYPE: DNA
```

```
<213> ORGANISM: Artificial Sequence
<220> FEATURE:
<221> NAME/KEY: misc_feature
<222> LOCATION: (1)..(2)
<223> OTHER INFORMATION: chalcone derivative based on benzylidenephenone between
      position 1 and 2
<221> NAME/KEY: source
<222> LOCATION: (1)..(19)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 3
aagcgcgcaa agacaaaat                                                  19

<210> SEQ ID NO 4
<211> LENGTH: 19
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: 5' end labeled with 32P phosphate
<221> NAME/KEY: source
<222> LOCATION: (1)..(19)
<223> OTHER INFORMATION: The artificial sequence is a synthetic oligonucleotide probe
      which was prepared with the beta-cyanoethylphosphoramidite
      method on an automated DNA synthesis instrument.
<221> NAME/KEY: misc_feature
<222> LOCATION: (18)..(19)
<223> OTHER INFORMATION: chalcone derivative based on benzylidenephenone between
      position 18 and 19

<400> SEQUENCE: 4
attttgtctt tgcgcgctt                                                  19

<210> SEQ ID NO 5
<211> LENGTH: 27
<212> TYPE: DNA
<213> ORGANISM: Artificial Sequence
<220> FEATURE:
<221> NAME/KEY: misc_feature
<222> LOCATION: (26)..(27)
<223> OTHER INFORMATION: coumarin derivative based on 3-O-(7-coumarinyl)-glycerol
      between position 26 and 27
<221> NAME/KEY: source
<222> LOCATION: (1)..(27)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 5
tctaggttca tgacaagctc gtcagaa                                         27

<210> SEQ ID NO 6
<211> LENGTH: 34
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: 5' end labeled with 32P phosphate
<221> NAME/KEY: source
<222> LOCATION: (1)..(34)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 6 tttttcctc aagagcattg taagcagaag actt                                  34
```

```
<210> SEQ ID NO 7
<211> LENGTH: 27
<212> TYPE: DNA
<213> ORGANISM: Artificial Sequence
<220> FEATURE:
<221> NAME/KEY: misc_feature
<222> LOCATION: (26)..(27)
<223> OTHER INFORMATION: chalcone derivative based on benzylidenephenone between
      position 26 and 27
<221> NAME/KEY: source
<222> LOCATION: (1)..(27)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 7
tctaggttca tgacaagctc gtcagaa                                              27

<210> SEQ ID NO 8
<211> LENGTH: 33
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: 5' end labeled with 32P phosphate
<221> NAME/KEY: source
<222> LOCATION: (1)..(33)
<223> OTHER INFORMATION: The artificial sequence is a synthetic oligonucleotide probe
      which was prepared with the beta-cyanoethylphosphoramidite
      method on an automated DNA synthesis instrument.
<221> NAME/KEY: misc_feature
<222> LOCATION: (4)..(5)
<223> OTHER INFORMATION: chalcone derivative based on benzylidenephenone between
      position 4 and 5

<400> SEQUENCE: 8
tttttcctca agagcattgt aagcagaaga ctt                                       33

<210> SEQ ID NO 9
<211> LENGTH: 55
<212> TYPE: DNA
<213> ORGANISM: Artificial Sequence
<220> FEATURE:
<221> NAME/KEY: source
<222> LOCATION: (1)..(55)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 9
taagtcttct gcttacaatg ctcttgaggc tgacgagctt gtcatgaacc tagat              55

<210> SEQ ID NO 10
<211> LENGTH: 27
<212> TYPE: DNA
<213> ORGANISM: Artificial Sequence
<220> FEATURE:
<221> NAME/KEY: misc_feature
<222> LOCATION: (26)..(27)
<223> OTHER INFORMATION: R enantiomer of coumarin derivative based on
      3-O-(7-coumarinyl)-glyerol between position 26 and 27
<221> NAME/KEY: source
<222> LOCATION: (1)..(27)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 10
tctaggttca tgacaagctc gtcagaa                                              27
```

```
<210> SEQ ID NO 11
<211> LENGTH: 27
<212> TYPE: DNA
<213> ORGANISM: Artificial Sequence
<220> FEATURE:
<221> NAME/KEY: misc_feature
<222> LOCATION: (26)..(27)
<223> OTHER INFORMATION: chalcone derivative based on benzylideneacetone
      between position 26 and 27
<221> NAME/KEY: source
<222> LOCATION: (1)..(27)
<223> OTHER INFORMATION: The artificial sequence is a synthetic oligonucleotide probe
      which was prepared with the beta-cyanoethylphosphoramidite
      method on an automated DNA synthesis instrument.

<400> SEQUENCE: 11
tctaggttca tgacaagctc gtcagaa                                    27
```